(12) United States Patent
da Silveira et al.

(10) Patent No.: US 6,881,421 B1
(45) Date of Patent: Apr. 19, 2005

(54) NANOPARTICLES COMPRISING AT LEAST ONE POLYMER AND AT LEAST ONE COMPOUND ABLE TO COMPLEX ONE OR MORE ACTIVE INGREDIENTS

(75) Inventors: Airton Monza da Silveira, Porto Alegre (BR); Gilles Ponchel, Paris (FR); Dominique Duchene, Paris (FR); Patrick Couvreur, Villebon sur Yvette (FR); Francis Puisieux, Maisons Alfort (FR)

(73) Assignee: Bioalliance Pharma S.A. (FR)

( * ) Notice: Subject to any disclaimer, the term of this patent is extended or adjusted under 35 U.S.C. 154(b) by 0 days.

(21) Appl. No.: 09/648,304

(22) Filed: Aug. 25, 2000

Related U.S. Application Data

(63) Continuation of application No. PCT/FR99/00418, filed on Feb. 24, 1999.

(30) Foreign Application Priority Data

Feb. 27, 1998 (FR) .............................. 98 02429

(51) Int. Cl.⁷ .............................. A61K 9/14; A61K 9/50
(52) U.S. Cl. ...................... 424/489; 424/499; 424/502
(58) Field of Search ................................ 424/489, 502, 424/499

(56) References Cited

U.S. PATENT DOCUMENTS

| | | | |
|---|---|---|---|
| 4,913,908 A | | 4/1990 | Couvreur et al. ........... 424/501 |
| 5,246,611 A | * | 9/1993 | Trinh |
| 5,641,515 A | * | 6/1997 | Ramtoola |
| 5,932,248 A | * | 8/1999 | Chen et al. |

FOREIGN PATENT DOCUMENTS

| | | |
|---|---|---|
| WO | WO 92/04916 | 4/1992 |
| WO | WO 93/25195 | 12/1993 |

OTHER PUBLICATIONS

Dominique Duchêne et al, "Cyclodextrins in targeting Application to nanoparticles," 1999, Advanced Drug Delivery Reviews, pp. 29–40, XP–002104026.

Airton Monza da Silveira et al, "Combined Poly(isobutylcyanoacrylate) and Cyclodextrins Nanoparticles for Enhancing the Encapsulation of Lipophilac Drugs," 1998, Pharmaceutical Research, vol. 15, No. 7, pp. 1051–1055, XP–002085312.

Elias Fattal et al, "Biodegradable polyalkylcyanoacrylate nanoparticles for the delivery of oligonucleotides," 1998, Journal of Controlled Release 53, pp. 137–143.

Niteen Bapat et al, "Uptake Capacity and Adsorption Isotherms of Doxorubicin on Polymeric Nanoparticles: Effect of Methods of Preparation," 1992, Drug Dev. Ind. Pharm., 18, pp. 65–77, XP–002085319.

Patrick Couvreur, "Polyalkylcyanoacrylates as Colloidal Drug Carriers," 1988, Crc Crit. Rev. Ther. Drug Carrier Syst., vol. 5, Issue 1, XP–002085327.

* cited by examiner

*Primary Examiner*—Barbara P. Badio
(74) *Attorney, Agent, or Firm*—DLA Piper Rudnick Gray Cary US LLP

(57) ABSTRACT

Nanoparticles containing at least one active ingredient including at least one polymer, preferably a poly (alkylcyanoacrylate), in which the alkyl group, linear or branched, contains from 1 to 12 carbon atoms, and of at least one compound able to complex said active ingredient. The invention also concerns the method for preparing these nanoparticles.

25 Claims, 10 Drawing Sheets

PARTICLE SIZE AND ZETA POTENTIAL OF NANOPARTICLES PREPARED IN THE PRESENCE OF HβCD

- ■ Granulometry of nanoparticles with 1% Poloxamer 188
- ☐ Granulometry of nanoparticles without Poloxamer 188
- ● Zeta potential of nanoparticles with 1% Poloxamer 188
- ○ Zeta potential of nanoparticles without Poloxamer 188

Initial HPβCD concentration (mg/ml)

NANOPARTICLES OF PIBCA / HPβCD PREPARED IN THE PRESENCE OF THE PROGESTERONE / HPβCD COMPLEX

- ■ Granulometry of nanoparticles with 1% Poloxamer 188
- □ Granulometry of nanoparticles without Poloxamer 188
- ● Zeta potential of nanoparticles with 1% Poloxamer 188
- ○ Zeta potential of nanoparticles without Poloxamer 188

HPβCD CONTENT IN FREE (NON-CHARGED) NANOPARTICLES

■ with 1% Poloxamer 188
□ without Poloxamer 188

Initial HPβCD concentration (mg/ml)

HPβCD CONTENT IN NANOPARTICLES PREPARED IN THE PRESENCE OF THE PROGESTERONE / HPβCD COMPLEX

■ with 1% Poloxamer 188
☐ without Poloxamer 188

PROGESTERONE CONTENT OF PIBCA / HPβCD NANOPARTICLES

■   with 1% Poloxamer 188

□   without Poloxamer 188

INFLUENCE OF PARTICLE SIZE ON THE RATE OF RELEASE OF PROGESTERONE IN ALKALINE BORATE BUFFER (ABB : pH 8.4) FROM PIBCA / HPβCD NANOPARTICLES

- ■ Progesterone solution
- □ HPβCD / progesterone in complex form
- ● nanoparticles of 150 nm (PIBCA / HPβCD)
- ○ nanoparticles of 70 nm (PIBCA / HPβCD)

Fig. 7 / A
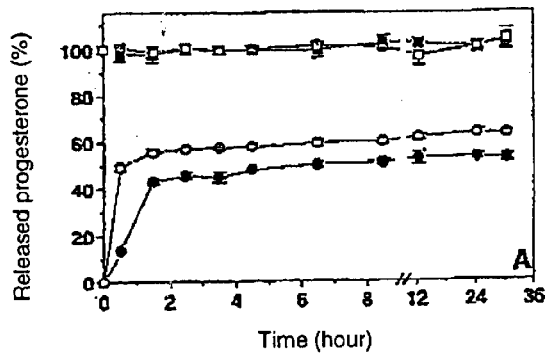
A = ABB : PEG 400 (80 : 20)
Fig. 7 / B
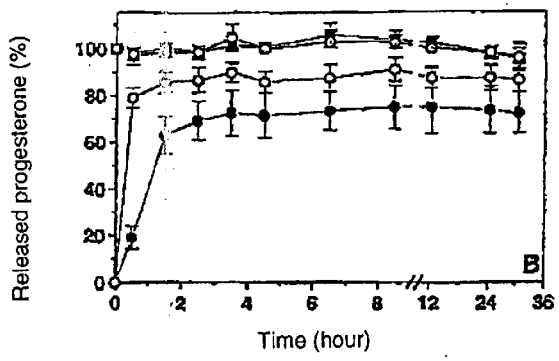
B = ABB : PEG 400 (60 : 40)
INFLUENCE OF THE CONSTITUTION OF THE RELEASE MEDIUM ON THE RELEASE RATE OF PROGESTERONE IN ABB MEDIUM (pH 8.4) FROM PIBCA / HPβCD NANOPARTICLES
- ■ Progesterone solution
- □ HPβCD / Progesterone in complex form
- ● nanoparticles of 150 nm
- ○ nanoparticles of 70 nm Fig. 8 / A
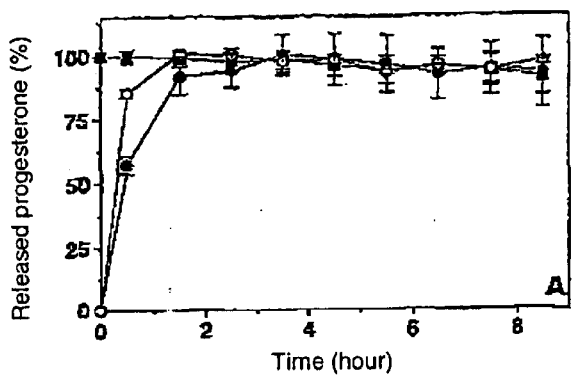
A = Esterase medium 25 IU
Fig. 8 / B
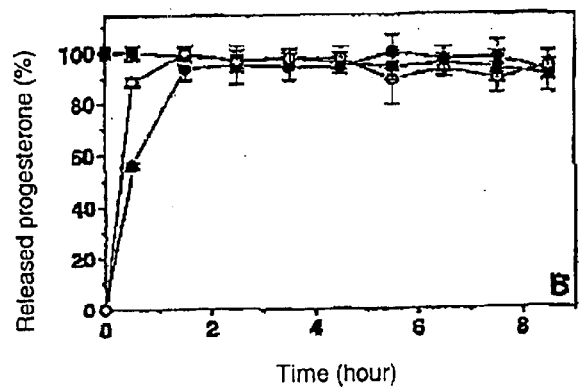
B = Esterase 100 IU
INFLUENCE OF THE PRESENCE OF ESTERASE-TYPE ENZYMES ON THE RELEASE RATE OF PROGESTERONE IN ABB MEDIUM (pH 8.4) FROM PIBCA / HPβCD NANOPARTICLES
- ■ Progesterone solution
- ☐ HPβCD / progesterone in complex form
- ● nanoparticles of 150 nm
- ○ nanoparticles of 70 nm RATE OF RELEASE OF HPβCD IN ABB MEDIUM (pH 8.4) FROM PIBCA / HPβCD NANOPARTICLES

- ■ nanoparticles of 150 nm
- ☐ nanoparticles of 70 nm

Fig. 10

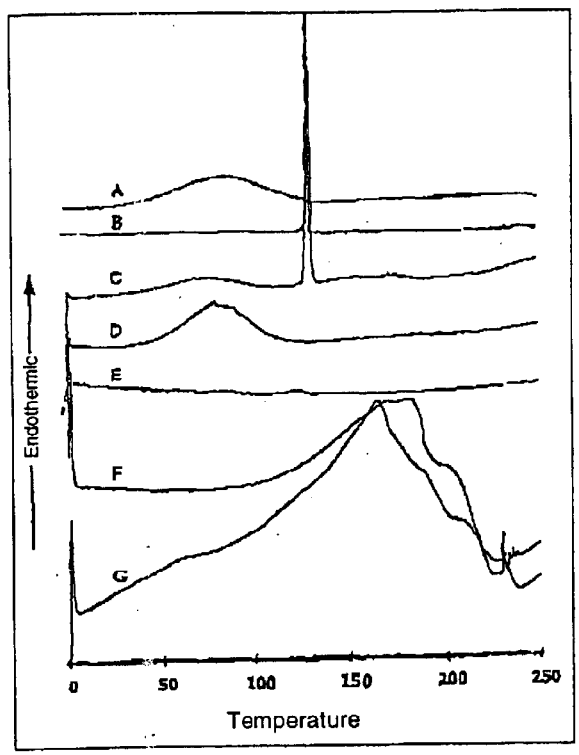

DIFFERENTIAL SCANNING CALORIMETRY (DSC) TRACINGS OBTAINED WITH A
TEMPERATURE RISE RATE OF 10°C / min.

A = HPβCD
B = Progesterone
C = Physical mixture of HPβCD Progesterone (5 : 1 W/W)
D = HPβCD : progesterone complex
E = PIBCA
F = Progesterone-containing nanoparticles of PIBCA / HPβCD (2.5 mg/ml HPβCD)
G = Progesterone-containing nanoparticles of PIBCA / HPβCD (10.0 mg/ml of HPβCD in medium).

NANOPARTICLES COMPRISING AT LEAST ONE POLYMER AND AT LEAST ONE COMPOUND ABLE TO COMPLEX ONE OR MORE ACTIVE INGREDIENTS

RELATED APPLICATION

This is a continuation of International Application No. PCT/FR99/00418, with an international filing date of Feb. 24, 1999, which is based on French Patent Application No. 98/02429, filed Feb. 27, 1998.

FIELD OF THE INVENTION

This invention relates to delivery of active ingredients used in the area of preventive, curative or diagnostic medicinal products and also relates to improvements in their therapeutic index (the benefit/risk ratio). More particularly, the invention relates to new nanoparticles containing at least one active ingredient.

BACKGROUND

A prime objective sought by the development of new delivery or release systems for active ingredients is the controlled delivery of an active agent, especially a pharmacological agent, to a site of action at an optimum rate and therapeutic dose. Improvements in therapeutic index may be obtained by modulating the distribution of the active ingredient in the body. Association of the active ingredient with a delivery system enables, in particular, its specific delivery to the site of action or its controlled release after targeting the action site. By reducing the amount of active ingredient in the compartments in which its presence is not desired, it is possible to increase the efficacy of the active ingredient, to reduce its toxic side effects and even modify or restore its activity.

Colloidal delivery systems for active ingredients include liposomes, microemulsions, nanocapsules, nanospheres, microparticles and nanoparticles. Nanoparticles offer the advantages of targeting, modulation of distribution and flexible formulation and have a polymer structure which may be designed and produced in a manner that is adapted to the desired objective. They have proved to be particularly promising for obtaining an improved therapeutic index as defined above due to their ability to ensure controlled release, specific delivery to the action site or targeted delivery allowing both an increase in efficacy and a reduction in toxic side effects on other organs.

This type of administration uses biodegradable polymers. Among these, poly(alkyl) cyanoacrylates) are of special interest since their bioerosion occurs rapidly in comparison with other biodegradable polymers and takes place during periods of time that are compatible with therapeutic or diagnostic applications.

Despite these characteristics of interest, the active ingredient content capacity of nanoparticles of poly (alkylcyanoacrylates), expressed in quantity of active ingredient associated with a mass unit of polymer, is often limited, especially when the active ingredient is only scarcely soluble in water since the production of nanoparticles uses polymerization techniques in an aqueous medium. This considerable limitation of the active ingredient content capacity is especially observed with hydrophobic, amphiphlic and/or insoluble active ingredients.

The relatively low ability of conventional nanoparticles to carry an adequate quantity of active ingredients from the administration site to the target site in the body often risks leading to the necessary administration of considerable quantities of polymers.

Poly(alkylcyanoacrylates) are used to produce nanoparticles as vectors of active ingredients. However, for the above-mentioned reasons, the low vectors loads obtained, especially with hydrophobic, amphiphilic and/or water insoluble active ingredients, restrict their therapeutic use.

BRIEF DESCRIPTION OF THE DRAWINGS

Various advantages and characteristics of the invention will become apparent with the description of the following examples which refer to the appended drawings in which:

FIG. 7 shows the influence of the constitution of the release medium on the release rate of progesterone in ABB medium (pH 8.4), from PIBCA/HPBCD nanoparticles.
  A: ABB: PEG 400 (80:20)
  B. ABB: PEG 400 (60:40)

FIG. 8 shows the influence of the presence of esterase-type enzymes on the release rate of progesterone in ABB medium (pH 8.4) from PIBCA/HPBCD nanoparticles.
  A: release medium with esterase 25 IU
  B: release medium with esterase 100 IU

FIG. 10 shows the tracings of differential scanning calorimetry (DSC) obtained with a rate of temperature rise of 10° C./min.

DETAILED DESCRIPTION OF THE INVENTION

Figure 1:
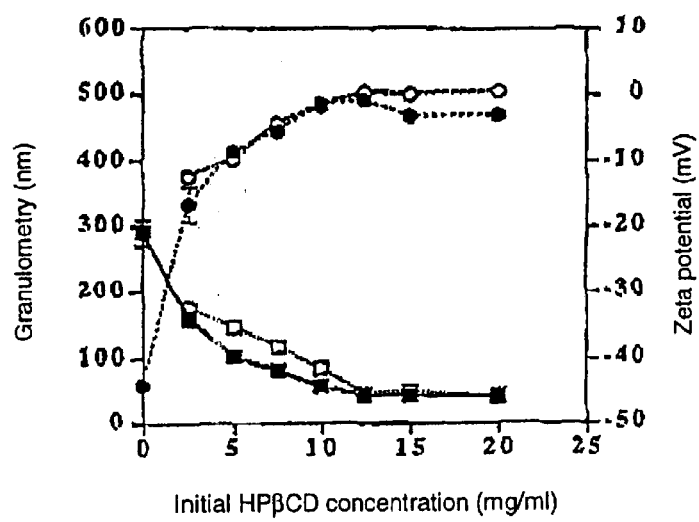
FIG. 1 shows variations in particle size, or granulometry, and in the zeta potential (average of three tests±SD) of nanoparticles of poly(isobutylcyanoacrylate) (PIBCA) prepared in the presence of 2-hydroxpyroyl-β-cyclodextrin (HPβCD) in relation to the initial concentration of HPBCD.

The following description is intended to refer to specific embodiments of the invention illustrated in the drawings and is not intended to define or limit the invention, other than in the appended claims.

In a surprising manner, it has now been found that is possible to widen the scope of use of polymers, in particular poly(alkylcyanoacrylates), by associating with them one or more compounds able to complex active ingredients and thereby obtain new nanoparticles having original properties.

The subject of the invention is, therefore, nanoparticles containing at least one active ingredient, comprising the association of at least one polymer, preferably a poly (alkylcyanoacrylate), in which the alkyl group, linear or branched, contains 1 to 12 carbon atoms, and of at least one compound able to form a complex with the active ingredient.

The compound able to complex the active ingredient according to the invention is preferably chosen from among the cyclical oligosaccharides, in particular, from among the cyclodextrins which may be neutral or charged, native (cyclodextrins α, β, γ,δ, ε), branched or polymerized, or even chemically modified, for example, by substitution of one or more hydroxypropyls by groups such as alkyls, aryls, arylalkyls, glycosidics, or by etherification, esterification with alcohols or aliphatic acids. Among the above groups, particular preference is given to those chosen from hydroxypropyl, methyl m, sulfobutylether groups.

In an unexpected manner, the presence of a compound able to complex the active ingredient in the association of the invention enables the active ingredient, even if it is hydrophobic, amphiphilic and/or insoluble, to penetrate inside the polymer structure resulting from association of the polymer or polymers and the compound or compounds able to complex the active ingredient, with an encapsulation yield within this structure that is significantly increased compared with the prior art. The yield appears to be related to the equilibrium between, firstly, solubilisation resulting from use of compounds able to complex the active ingredient and, secondly, affinity of the active ingredient for the new polymer structure, which brings substantial progress at therapeutic and industrial levels. Also, the nanoparticles also stabilize the complex formed between the compound(s) and the polymer(s) due to the solid nature of the nanoparticles.

Through the invention, it is now possible to load nanoparticles, for example, of the poly (alkylcyclanaoacrylate) type, not only with hydrophilic active ingredients, but also with hydrophobic, amphiphilic and/or insoluble active ingredients.

The association of a polymer with a compound able to complex the active ingredient brings the possibility of creating new fixation sites for the active ingredient which are not apparent with polymers used alone. Creation of these new sites, in particular, a hydrophobic cavity with compounds able to complex active ingredients makes it possible to increase the content load of active ingredient while maintaining its capacity for controlled and delayed release which is non-existent when compounds able to complex are used alone.

The prior art describes preparation of cyanoacrylate-containing polymers in which the alkylcyanoacrylates are associated with dextran during the preparation stage (Egea M. A. et al., Farmaco, 1994, 49, 211–17). In this method, however, dextran is conventionally used as a stabilizing agent and does not permit complexing of an active molecule. Also, dextran is a linear polysaccharide with high molecular weight and it is, therefore, fundamentally different from the cyclodextrins which have a low molecular weight and are able to complex other molecules. Therefore, the nanoparticles according to the present invention offer original properties:

modulation of their size, increased encapsulation of active molecules, especially hydrophobic, amphiphilic and/or insoluble molecules, and optional absence of stabilizer such as dextran.

U.S. Pat. No. 5,641,515 also describes the encapsulation of insulin with a polycyanoacrylate polymer. This encapsulation is based on formation of covalent bonds between insulin and the polymer, which is different from the nanoparticle-based "complex" of the present invention.

The nanoparticles of the invention are based on the ability of a molecule of an active ingredient to combine itself with one or more cyclodextrin molecules through the creation of low-energy chemical bonds, that are, hence, non-covalent such as to form an inclusion complex. The existence of this complex results from the formation of an equilibrium between a) the free forms of the active ingredient and cyclodextrin and b) the inclusion complex. It is quantitatively characterized by its stability constants. In the meaning of the present invention, the term "complexation" describes this latter phenomenon. Therefore, complexation of the active ingredient is implemented not only during preparation of the nanoparticles, but also in the prepared nanoparticles, in which it represents a means of associating a greater quantity of active ingredient.

It is helpful to recall that, in general, association of an active ingredient with nanoparticles may result from simple dispersion of the active ingredient in crystal form in the particle-forming polymer, from solubility of the active ingredient in the polymer, from adsorption bringing into action secondary chemical bonds (low-energy), or finally from a covalent bond (high-energy) with the particle-forming polymer.

In this respect, it is appropriate to point out that preparation of nanoparticles requires polymerization of the monomers of alkylcyanoacrylates dispersed in an aqueous phases. Synthesis of the poly(alkycyanoacrylate) then enables formation of the nanoparticles. Generally, this stage is conducted in the presence of the active ingredients to be encapsulated. It may, therefore, in some cases lead to the non-desired development of covalent chemical bonds between the active ingredient and the formed polymer. This phenomenon has been reported for peptides (Grangier J. I., J. Controlled Rel. 15, 3–13, 1991) or other molecules (vinblastin, V. Guise et al., Pharma. Res., 7, 736–741, 1990).

The present invention remedies this disadvantage since, by masking the potentially reactive chemical groups, complexation of the active ingredient during preparation of the nanoparticles of the invention makes it possible to protect the active ingredient against chemical reactions that are necessary for the formation of the particle. Therefore, the active ingredient is advantageously associated in a non-covalent manner with the particle.

Also, association of the active ingredient with nanoparticles is generally conducted in an acid aqueous medium. For some active ingredients, however, that are unstable under these conditions, there is a resulting risk of chemical degradation likely to lead to the non-desired encapsulation of hydrolysis derivatives which is, moreover, detrimental to obtaining a high encapsulation level of the active ingredient. On the other hand, in the present invention, complexation of active ingredients with cyclodextrins makes it possible to overcome these disadvantages as it enables the active ingredients to be protected against the outside reaction medium.

As examples of active ingredients which may enter into the composition of the nanoparticles of the invention, mention may be made of anticancer and antisense substances, antivirals, antibiotics, proteins, polypeptides, polynucleotides, antisense nucleotides, vaccinating substances, immunomodulators, steroids, analgesics, antimorphinics, antifungals, antiparasticids. Among the latter, the invention gives particular consideration to taxol or one of its derivatives, doxorubicin or one of its derivatives, platinum derivatives.

The active ingredient is generally present in a quantity of about 0.01 to about 300 mg/g of nanoparticles.

The proportion of compound able to complex the active ingredient is in general from about 0.1 to about 70% by weight.

The proportion of active ingredient and the proportion of compound able to complex are independent from one another.

The invention also relates to pharmaceutical or diagnostic compositions comprising the nanoparticles of the invention and at least one vehicle that is pharmaceutically acceptable and compatible.

A first method of preparing nanoparticles containing a polymer, more particularly, a poly(alkylcyanoacrylate) as defined above, is characterized in that it comprises:

a) preparing a complex of at least one active ingredient with at least one compound able to complex the latter, in solution in an aqueous or non-aqueous solvent, b) gradually adding at least one monomer of the polymer, more particularly, the alkylcyanoacrylate monomer, in the solution obtained at step (a), and c) conducting polymerization, preferably anionic, but also inducible by other, especially photochemical, agents of this monomer, optionally in the presence of one or more surfactant and/or stabilising agents.

A second method of preparing the nanoparticles of the invention, forming an alternative to the above method, comprises, firstly, preparing nanoparticles containing a polymer, more particularly poly(alkylcyanoacrylates), and a compound able to complex an active ingredient, also called "blank nanoparticles", then associating the active ingredient with the blank nanoparticles. More particularly, this method comprises:

a) preparing a solution of at least one compound able to complex an active ingredient in an aqueous or nonaqueous solvent, b) gradually adding at least one monomer of the polymer, more particularly the alkylcyanoacrylate monomer, to the solution of step (a), c) conducting polymerization, preferably anionic but also inducible by other agents, in particular photochemical agents, of this monomer, optionally in the presence of one or more surfactant and/or stabilising agents, and d) after controlling and optionally purifying the nanoparticles obtained at step (c), incubating the particles in a solution of the active ingredient in an aqueous or non-aqueous solvent.

As in the first method, the association of the active ingredient with the blank nanoparticles is dependent upon the quantity of cyclodextrins associated with the nanoparticles. This second method offers at least two advantages:

it avoids having to conduct purification stages on the nanoparticles loaded with active ingredient, which may lead to active ingredient losses, and it enables a system to be produced which may be extemporaneously loaded with active ingredient, for example, when the active ingredient is very unstable in solution.

The invention, therefore, also relates to blank nanoparticles, that is to say non-loaded nanoparticles, obtained after steps (a) to (c) in the second above-described method. Also, these blank particles are of therapeutic interest due to the activity of the cyclodextrins especially in the area of cancer treatment.

During steps (a) and (b) of the first method of the invention, the solvent is advantageously chosen such that, while maintaining conditions propitious to polymerization of the polymers, of (poly)alkylcyanoacrylates in particular, the solubility of the active ingredient and of the compound able to complex is maximized in the medium defined by this solvent. Advantageously, the solvent is preferably chosen from among aqueous or hydroalcoholic solvents. The solvent is chosen in the manner described for steps (a), (b) and (d) of the second method of the invention.

The presence of a surfactant or stabilising agent is necessary to prepare the nanoparticles of the prior art. The following examples demonstrate that such agents are not necessary for the present invention. The compound able to complex the active ingredient, such as cyclodextrins, paradoxically have a sufficient stabilising effect for the surfactant agent usually used to be omitted. On an industrial scale, this represents a significant savings. Also it is observed tat poly(alkylcyanoacrylate) stabilizes the complex made up of the active ingredient and the compound able to complex the active ingredient.

However, if the method of the invention entails using a stabilizing and/or surfactant agent, preference is given to a dextran or a poloxamer.

According to one preferred embodiment of the invention, the potentialities of the cyclodextrins vis-a-vis the active ingredients allow new properties to be added to the particles. The presence of cyclodextrins in the particles enables stabilization of the active ingredients which would be unstable in solution, or even the masking of some unfavorable characteristics of the active ingredients such as an irritant action.

The production methods for nanoparticles known to date have shortcomings concerning the possibilities of size adjustment of the nanoparticles. In an unexpected and remarkable manner, with the method of invention it is possible to adjust nanoparticle size directly during their production with no special additional stage.

As is shown in the following examples, the size of the nanoparticles of the invention is essentially related to the concentration of the compound able to complex the active ingredient. For cyclodextrins, this size can be varied over a very wide range from about 300 to less than about 50 NM. Through the invention, therefore, using simple preliminary tests, it is possible to adjust nanoparticle size in the compositions of the invention, especially pharmaceutical compositions, depending upon the special desired effect. In theory, having a choice of size, it is subsequently possible, if so desired, to overcome some physical obstacles to the distribution of nanoparticles in the body, or to prevent capture of the nanoparticles of the composition by the reticuloendothelial system. It also enables new targeting of organs.

Consequently, at step (a) of the method of the invention the proportion of compound able to complex the active ingredient is generally from about 0.1 to about 70% by weight in relation to the active ingredient. As indicated above, the choice of concentration of the compound able to complex the active ingredient makes it possible to vary the size of the nanoparticles obtained with the method of the invention. Nanoparticles with a size of between about 40 and about 300 NM can be obtained.

Studies on the release of the compound able to complex the active ingredient and release of the active ingredient show that the release curve of the compound able to complex the active ingredient is very rapid and that release is close to 100%, while release of the active ingredient comprises a first rapid stage followed by a slower second stage due to bioerosion, conventional described in respect of poly (alkylcyanoacrylates).

In active ingredient release tests, use of esterases, which deteriorate the nanoparticles, shows that the active ingredient is largely contained in the nanoparticle matrix network, which is of importance from the viewpoint of expected activity.

Different tests conducted on a range of steroids, from the most hydrophilic (hydrocortisone) to the most hydrophobic (progesterone), have shown that varied active ingredients may be contained in the nanoparticles of the invention at high concentrations depending upon their physico chemical characteristics such as their degree of hydrophobicity in particular.

For example, the progesterone used as a model in the following examples has very low water-solubility (0.01 mg/ml) which, in conventional emulsion-in-water polymerization methods, can only lead to obtaining a very low active ingredient content that is of no practical advantage. Therefore, this content is low when preparation techniques of the prior art are used. In a particularly surprising and interesting manner, this content is more than about 50 times higher in the nanoparticles of the invention. The invention, therefore, gives access to hydrophobic, amphiphilic and/or insoluble active ingredients and, hence, to a change in their therapeutic index.

A further purpose of the invention is therefore the use of the above-described methods to produce a medicinal product having a targeted effect and an improved therapeutic index.

EXAMPLES

In the following examples, isobutylcyanoacrylate, hydrocortisone, prednisolone and danazol, progesterone and esterases (19 IU/ml) were obtained from Sigma Chemicals (St. Louis, Mo. USA), spironolactone, testosterone, megestrol acetate were obtained respectively from Sophartex, Besin-Iscovesco and Upjohn, α- β- and γ-cyclodextrins, 2-hydroxypropyl-α-, 2-hydroxypropyl-β- and 2-hydroxypropyl-γ-cyclodextrins, with average MS values of respectively 0.9, 0.6 and 0.6 were obtained from Wacker Chemie BmbH (Munich, Germany) and sulfobutyl β-cyclodextrin ether (hereinafter SBEβCD) was obtained from CyDex L. C. (Overland Park, Kans., USA). Poloxamer 188 (Lutrol F68®) was a donation from BASF (Ludwigshafen, Germany). The other chemical products and solvents are of analytical and HPLC grade.

Example 1

Preparation of nanoparticles in the presence of different cyclodextrins and poloxamer.

The nanoparticles were prepared by anionic polymerization of 100 μl isobutylcyanoacrylate in 10 ml 0.01 M hydrochloric acid (pH 2.0) containing 1% w/v poloxamer 188 and in the presence of 5 mg/ml (α-, β-, γ-, 2-hydroxypropyl-α-, 2-hydroxypropyl-β- or 2-hydroxypropyl-γ-cyclodextrin or sulfobutyl β-cyclodextrin ether. The cyclodextrin solution was magnetically stirred (1000 r/min) at ambient temperature and the monomer added drop by drop. After stirring for 6 hours, the suspension was filtered through a 2.0 μm prefilter (Millex AP 500®) and then further characterized.

Example 2

Preparation of nanoparticles in the presence of different cyclodextrins.

The nanoparticles were prepared by anionic polymerization of 100 μl isobutylcyanoacrylate in 10 ml 0.01 M hydrochloric acid (pH 2.0) in the presence of 5 mg/ml of α-, β-, γ-2-hydroxypropyl-α-, 2-hydroxypropyl-β- or 2-hydroxypropyl-γ-cyclodextrin or sulfobutyl β-cyclodextrin ether. The cyclodextrin solution was magnetically stirred (10 OOr/min) at ambient temperature and the monomer added drop by drop. After stirring for 6 hours, the suspension was filtered through a 2.0 μm prefilter (Millex AP 500®) and then further characterized.

Example 3

Preparation of progesterone/hydroxyvipropyl-β-cyclodextrin (HPBCD) complexes.

The progesterone/HPβCD complexes were prepared by mixing 3.615 g HPβCD with 3.0 g progesterone in 150 ml water under magnetic stirring for 24 hours at ambient temperature. Afterwards, the mixture was filtered (0.45 μm). The HPβCD and progesterone were titrated in the filtered solution before being used for the preparation of progesterone-containing nanoparticles.

Example 4

Preparation of nanoparticles of (poly) isobutylcyanoacrylate/HPβCD (PIBCA/HPβCD) containing progesterone.

The solution of the progesterone/HPβCD complex obtained as described in example 3 was diluted to obtain concentrations of 2.5, 5.0, 7.5, 10,0, 12.5, 15.0 and 20.0 mg/ml of HPβCD in the polymerization medium. The nanoparticles were prepared as in Example 1, in the absence of presence of 1% (w/v) of poloxamer 188.

Example 5 (reference):

Preparation of nanoparticles of poly (isobutylcyanoacrylate) containing progesterone with no HPβCD.

Nanoparticles of poly(isobutylcyanoacrylate) were prepared in the absence of cyclodextrin in the polymerization medium, to act as a reference. The progesterone-containing nanoparticles were prepared by dissolving the active ingredient in diluted hydrochloric acid (pH 2.0) in the presence of 1% (w/v) of poloxamer 188 (approximately 60 μg/ml), corresponding to maximum solubility in this medium). The polymerization process was implemented as described in Example 1.

Example 6

Titration of progesterone and HPβCD in the nanoparticles obtained.

The different suspensions of nanoparticles were centrifuged at 82,000 g for 30 to 40 min at 25° C. (Beckman, L5-65 Ultracentrifuge, 70.1 Ti type rotor) and resuspended in 5 ml distilled water. The suspensions were finally freeze-dried (Christ HED Freeze Drier, Germany).

To titrate the progesterone content in the nanoparticles, the freeze-dried products were diluted in acetonitrile of HPLC grade and the solutions analyzed by high performance liquid chromatography (HPLC). The HPLC system consisted of a 510 solvent delivery unit (Waters-Saint-Quentin-en-Yvelines, France), a WISP 712 automatic sampler, a column Nova-Pak C18 4 μm column (250×4.6 mm), a 486 absorbency detector which operated at 245 NM and interfaced with a 746 data module. The flow rate was 1.0 ml/min and the mobile phase made up of water and acetonitrile (40:60) for which the retention time was approximately 12 min. The results were expressed as an average of three titrations.

For quantification of HPβCD, the freeze-dried nanoparticles were hydrolyzed with 0.2 M NaOH for 12 hours, the pH adjusted to 7.0 (±0.5) and the HPBCD quantified by spectrophotometric titration of the discoloring of phenolphthalein solutions in the presence of HPβCD. Phenolphthalein formed stable, colorless inclusion complexes with cyclodextrins (CD). Consequently, the color intensity of a phenolphthalein solution in alkaline borate buffer decreased in proportion to the quantity of CD in solution.

Reference solutions were prepared by diluting mother solutions of CD in alkaline borate buffer solution with pH 10.0 containing 2% ethanol solution of 0.006 M phenolphthalein. The reference curves (λ=550 nm) are linear for CD concentrations ranging from 1 to 100 μg/ml. To the samples were added 4 parts buffer solution containing phenolphthalein and they were then tested directly.

Example 7

Characterization of the nanoparticles.

Granulometric distribution, average size and polydispersity of the nanoparticles were estimated by laser light diffusion using an NS Coulter Nanosizer (Coultronics, Margency, France). The samples were dispersed in MilliQ water (resistivity >18 MΩ, Millipore, Saint-Quentin-en-Yvelines, France). Each analysis lasted 200 s. The temperature is 20° C. and the analysis angle was 90°. The zeta potential of the particles in suspension in MilliQ water was determined by Doppler laser velocimetry (Zetasizer 4, Malvern, England).

Results of Example 1 to 7

The characteristics of the particles prepared in the presence of 5 mg/ml of different cyclodextrins and 1% poloxamer 188 (average of 3 repeated preparations ±SD) are grouped in table I below.

TABLE I

| CD (5 mg/ml) | Size (nm) ± S.D. | ζ potential (mV) ± S.D. | CD content (mg CD/mg nanoparticles) |
|---|---|---|---|
| alpha | 228 ± 69 | −34.4 ± 4.0 | ND |
| beta | 369 ± 7 | −24.7 ± 8.2 | 360 |
| gamma | 286 ± 9 | −22.9 ± 0.6 | 240 |
| HPalpha | 244 ± 25 | −27.0 ± 2.2 | ND |
| HPbeta | 103 ± 6 | −8.6 ± 0.9 | 247 |
| HPgamma | 87 ± 3 | −2.6 ± 2.2 | 220 |
| SBEbeta | 319 ± 10 | −45.4 ± 2.4 | ND |

CD = Cyclodextrin
HP = Hydroxypropyl
SBE = Sulfobutyl ether

Particle size, zeta potential, cyclodextrin content and stability (values not given) were influenced by the nature of the cyclodextrin.

The quantity of the different cyclodextrins bonded to the particles lies in the range of about 20 to about 35% (w/w) of total particle weight.

The nanoparticles formulated with HEβCD offer the most interest as they have an average granulometry of less than about 100 nm and a zeta potential close to zero mV. Also, HPβCD offers very extensive solubility in the polymerization medium and excellent tolerability. It also enables the encapsulation of numerous substances. Consequently, additional studies were conducted on HPβCD.

In the presence of HPβCD in the polymerization medium, the addition of the poloxamer 188 surfactant agent is not essential for the production of nanoparticles.

First, as shown in FIG. 1, the size and zeta potential of the particles are not modified by the presence of poloxamer 188.

Figure 2:
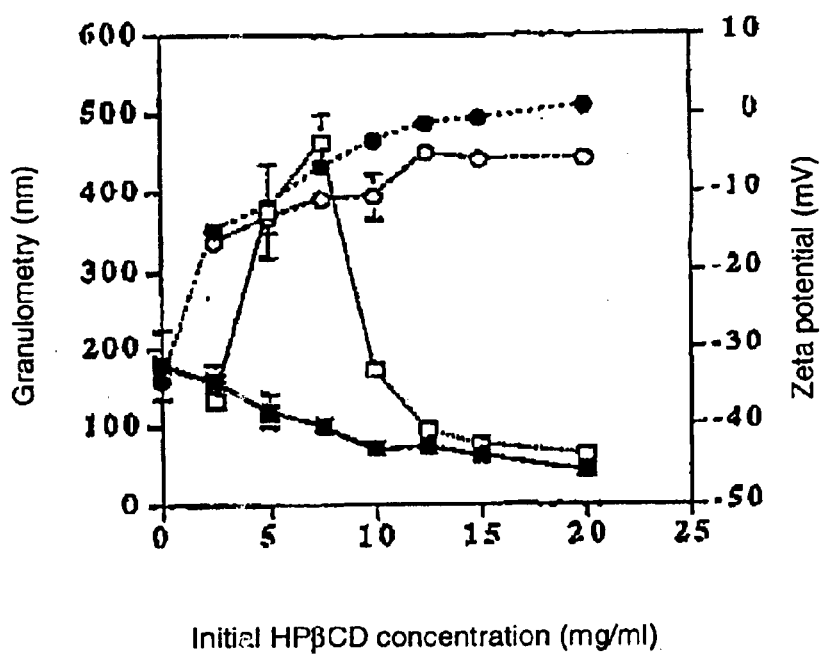
FIG. 2 shows variations in granulometry and zeta potential (average of three tests±SD) of PIBCA nanoparticles prepared in the presence of the progesterone complex: 2-hydroxypropyl-β-cyclodextrin (HPβCD), relative to the initial concentration of HPβCD.

Second, the concentration of HPβCD has a considerable influence on size and zeta potential. An increase in HPβCD concentration from 0 to 12.5 mg/ml leads to a reduction in particle size from 300 nm. to less than 50 nm. Also, the zeta potential of the particles gradually decreases from strongly negative values (−40 mV) to a surface potential close to 0 mV. These trends are generally maintained when the nanoparticles are prepared in the presence of progesterone as shown in FIG. 2.

Figure 3:
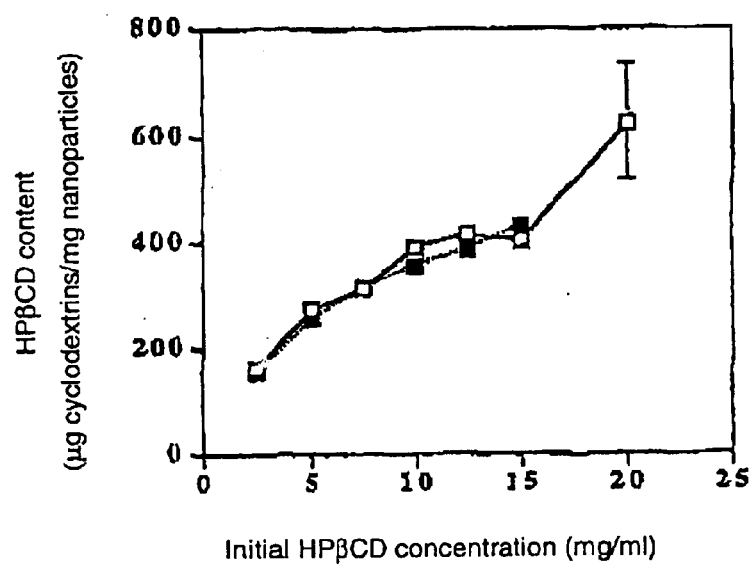
FIG. 3 shows variations of HPβCD content (average of three tests±SD) of PIBCA nanoparticles prepared in the presence of HPβCD, in relation to the initial concentration of HPβCD.

Compared with the particles not containing progesterone, the zeta potential is slightly negative in the HPβCD concentration range being studied. Also, in the absence of poloxamer 188, a rapid increase is observed in nanoparticle size, up to about 450 nm, followed by a rapid decrease when the HPβCD concentration is greater than 10 mg/ml. This phenomenon does not occur in the presence of poloxamer 188. The addition of HPβCD to the polymerization medium leads to the association of larger quantities of HPβCD with the nanoparticles, as is shown in FIG. 3.

Figure 4:
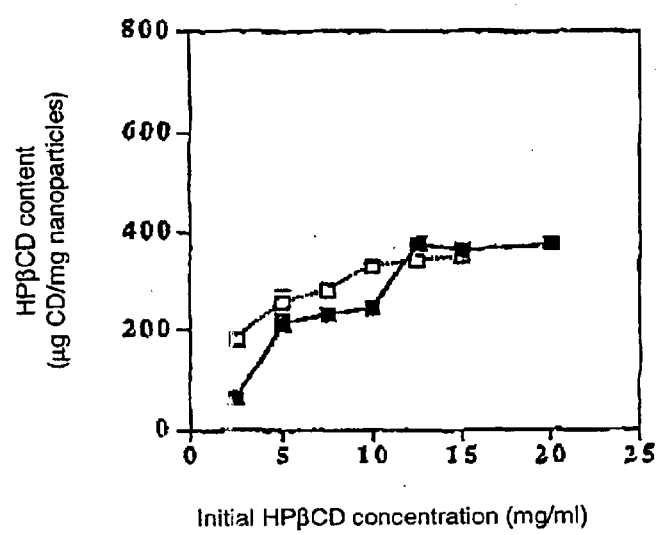
FIG. 4 shows variations in HPβCD content (average of three tests±SD) of PIBCA nanoparticles prepared in the presence of the progesterone: HPBCD complex, in relation to the initial concentration of HPβCD.
Figure 5:
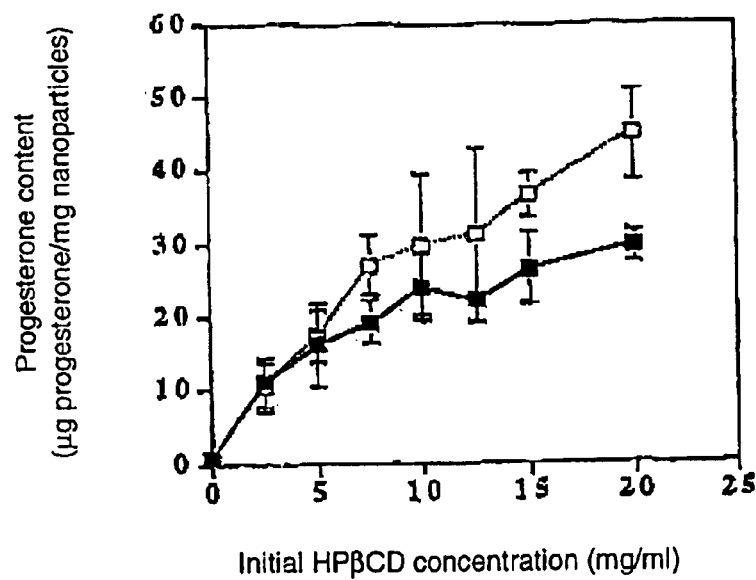
FIG. 5 shows variations in progesterone content (average of three test±SD) of PIBCA/HPβCD nanoparticles, in relation to the initial concentration of HPβCD.

The quantity of HPβCD associated with the particles continuously increases and may reach about 60% of particle weight. When the initial masses of HPβCD and isobutylcyanoacrylate in the polymerization medium are equal, the quantity of HpβCD associated with the particles is approximately 35%. Also, the association of HPβCD with the particles is not influenced by the presence of poloxamer 188. The HPβCD content of the nanoparticles is not considerably affected by the presence of progesterone in the polymerization medium, as is shown in FIG. 4. The progesterone content of the particles increases in spectacular fashion when the particles are prepared in the presence of HPβCD. The progesterone content, in the absence of HPβCD is 0.79 μg/ml of particles, and it gradually increases until it is multiplied by 50, which corresponds to 45 μg/mg of particles, as is shown in FIG. 5. There are no significant differences between the particles prepared with or without poloxamer 188.

The characteristics of the nanoparticles used in following Examples 8 to 10 are described in Table II below.

TABLE II

| Formulation[a] | Size (nm) ± SD | HPβCD content[b] | Active ingredient content[c] |
|---|---|---|---|
| 2.5 | 158 ± 22 | 64 ± 5.4 | 10.0 ± 3.3 |
| 10.0 | 70 ± 5 | 240 ± 7.6 | 23.9 ± 4.4 |

[a] = initial HPβCD concentration in the polymerization medium (mg/ml)
[b] = μg of HPβCD per mg of nanoparticles
[c] = μg of progesterone per mg of nanoparticles Example 8

In vitro release of progesterone from nanoparticles of PIBCA/HPBCD

A weighed quantity of freeze-dried nanoparticles (containing 1% (w/v) of glucose) was placed in a bottle containing 15 ml of alkaline borate buffer solution (ABB)

(pH 8.4) or of ABB containing esterases (25 and 100 IU) or of ABB/poly(ethyleneglycol) 400 (PEG) at 20 and 40% (v/v). The samples were magnetically stirred at 200 r/min and 37° C., and taken at predetermined intervals. The suspensions were centrifuged at 82,000 g for 30 minutes at 20° C., then the progesterone content of the supernatant is determined for all media and the HPβCD content for the PEG media. The progesterone content is determined using HPLC as described above with injection of 100 µl for the samples incubated in ABB media and 20 µl for the PEG media.

All the tests are conducted under conditions such 15 that the active ingredient concentration during the release stage is maintained below 10% saturation.

Example 9

In vitro release of HP5CO from nanoparticles of HpβCD/ from nanoparticles of PIBCA/HPBCD Study of the release of HPBCD was conducted as for progesterone in ABB medium with quantification of the CD content after ultracentrifuging, by complexation with phenolphthalein as described above. The CD concentration at 100% release was approximately 100 µg/ml.

Example 10

Differential scannina calorimetry (DSC)

DSC studies were conducted using a Perkin Elmer DSC-7 differential scanning calorimeter. The temperature was calibrated using the melting transition point of indium. Samples weighing approximately 4 mg were placed in 30 aluminum capsules and heated from 0 to 250° C. at an investigation rate of 10° C./min.

Results of Examples 8 to 10

Figure 6:
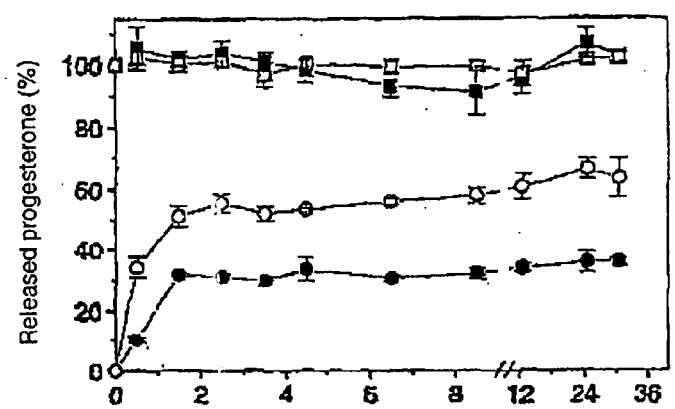
FIG. 6 shows the influence of particle size on the release rate of progesterone in alkaline borate buffer (ABB) (pH 8.4) from PIBCA/HPBCD nanoparticles.

FIG. 6 in the appended drawings shows the release curve of progesterone from combined PIBCA/HPβCD nanoparticles in ABB (pH 8.4). In this graph a bi-phase release curve can be seen with initial rapid release (scattering effect) during the first hour for both tested formulations (approximately 10 and 34% of nanoparticles of 150 and 70 nm respectively). This rapid release can be attributed to the fraction of progesterone which is adsorbed or weakly bonded to the large surface generated by the formation of nanoparticles rather than to the progesterone/CD complex incorporated in the polymer network. The second phase corresponds to slower exponential release with approximately 35 and 62% of progesterone released from nanoparticles of 150 and 70 nm, respectively. This slower release phase may be the result of simple outward-moving diffusion of progesterone from the nanoparticles, or of penetration of the release solution into the nanoparticles with dissolution of the progesterone followed by its outgoing diffusion.

In vitro studies show that different factors may affect the release of active ingredients from colloidal systems. These factors include particle size and morphology, active ingredient content and its solubility. In accordance with observations made in previous work, the smallest nanoparticles (70 nm) with a higher active ingredient content (24 µg/mg) give faster release than larger particles (170 nm) with a lower progesterone content (10.5 µg/mg). Average size and active ingredient content of the nanoparticles are the major factors for rate of release with a reduction in the rapid phase for the larger-sized particles.

FIG. 7 shows the release curves for progesterone from nanoparticles of PBICA/HPβCD in the presence of PEG 400 (20 and 40%) as a solubilising agent. The use of this type of medium makes it possible to reduce the volume of release medium and, consequently, the concentration of active ingredient for improved detection. In this type of case, in which non-aqueous solvents or solubilising agents are used, it is possible to obtain information on the release mechanism. As shown in FIG. 7, the release curve is not identical for these two media, which means that release is strongly influenced by PEG concentration. Consequently, the release of progesterone is determined by penetration of the solvent into the polymers matrix, which dissolution and outside diffusion of the active ingredient from the nanoparticles. On the contrary, when the release of active ingredient results from mere diffusion across the polymer matrix, the composition of the release solvent cannot influence release of the active ingredient.

The method for preparing nanoparticles which consists of adding the monomer to an aqueous solution of surfactant agent and of stirring to obtaining micelles can determine the distribution of the active ingredient in the micelles during the polymerization stage.

The rapid release observed in FIGS. 6 and 7 suggests that the surface of the particles was enriched with progesterone during the polymerization stage. Also, a high proportion of active ingredient may have been trapped in the polymer network which could have a highly porous inner structure. This could account for the increase in release rate when the PEG concentration increases (FIG. 7), with the PEG penetrating inside the structure at different rates depending upon the constitution of the release medium, and then modifying diffusion of the active ingredient towards the outside.

Despite a very substantial increase in the release rate obtained with the addition of PEG to the release medium, the release of progesterone does not attained 100% (it is approximately 75 and 82%, respectively, with 40% PEG).

On the contrary, the presence of esterase-type enzymes in release medium leads to faster release than in a release solution not containing esterases, and the quantity of release progesterone is very close to 100% for the two tested formulations and for both enzyme concentrations (FIG. 8). These facts could suggest that the progesterone molecules are, at least in part, trapped in molecular state in the polymer matrix of the nanoparticle of the invention and/or are bound to the isobutylcyanoacrylate network. The use of esterase-type enzymes in the release medium leads to degradation or dissolution of the polymer chains of the poly(cyanoacrylate) nanoparticles. In this case, the active ingredients immobilized in the matrix are released by gradual degradation of the matrix.

Figure 9:
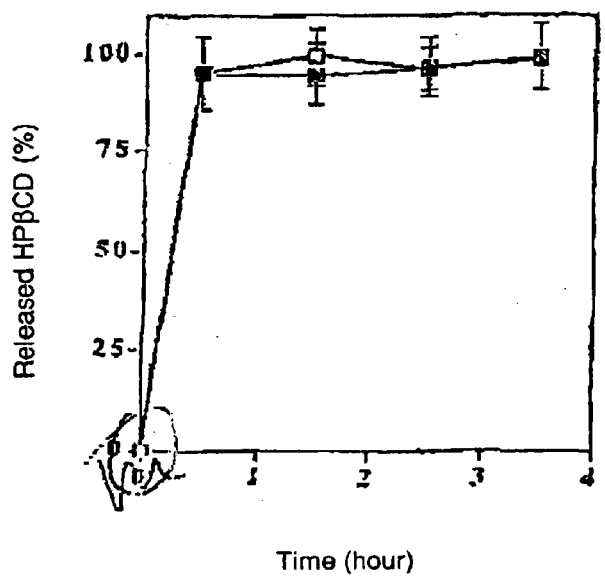
FIG. 9 shows the release rate of HPβCD in ABB medium at 37° C.

The bioerosion caused by hydrolysis of the ester bond of the PIBCA side chains is the mechanism which enables significant acceleration in the release of progesterone, which tallies with the results reported by others. At times, on the release of active ingredients in media containing esterases do not lead to 100% release of the incorporated active ingredient. It is suggested that there then exists the possibility of a bond between the PIBCA chains and the molecules of the active ingredient. The release curves of cyclodextrin from nanoparticles shown in FIG. 9, show a very rapid release, very close to 100% during the first hour, which demonstrates that these molecules are not chemically bound to the polymer, but most probably are simply adsorbed or trapped in the polymer.

DSC tracings of samples containing HPβCD show a wide endothermic transition, reproducible in the 30 to 90° C. range with initial temperatures lying within this range (FIGS. 10a, c and d). This asymmetrical peak has been attributed to the removal of water. The samples containing progesterone (physical mixture and progesterone alone) show a marked endothermic peak at approximately 130° C. which corresponds to the melting transition point of progesterone in crystalline form (FIGS. 10b and c). The HPBCD: progesterone complex only shows endothermic transition in the above-described 30 to 90° C. range, with disappearance of the melting transition of the crystalline form of progesterone (FIG. 10d) which suggests that the active ingredient is dispersed in the molecular state within the cavity of the cyclodextrin molecules. In the same form, samples of PIBCA/HPβCD particles containing progesterone do not show a marked endothermic peak which, in this case, is replace by a wide endothermic transition in the range of about 130 to about 170° C. (FIGS. 10e and f). This phenomenon suggests that the progesterone is in the molecular state, either dissolved in the polymer or included in the cyclodextrins associated with the nanoparticles of the invention.

In this form, all the results relating to the release of cyclodextrin and progesterone in the different media and the DSC curves, plus the data in the literature, indicate that the morphology of the nanoparticles could be represented by a polymer nucleus containing a fraction of active ingredient in the molecular state, with a surface enriched with cyclodextrin progesterone complexes. This structure could account for the bi-phase release of progesterone with a first rapid phase perhaps due to desorption of the cyclodextrin: progesterone complex from the surface, and a second very slow phase entailing the outside diffusion of the progesterone across the polymer network.

Example 11

Preparation of nanoparticles of poly (isobutylcyanoacrylate)/HPβCD containing various active ingredients.

Complexes of prednisolone, spironolactone, testosterone, progesterone, danazol and megestrol acetate were obtained by mixing 300 mg HPβCD with 15 mg steroids in 15 ml water at 37° C. for 72 hours under magnetic stirring. The suspensions were filtered (0.45 mm) and the cyclodextrin and active ingredient concentrations were determined as in Example 12 below. Nanoparticles of poly (isobutylcyanoacrylate)/HPβCD are prepared as in Example 1 by adding a solution of formed complexes containing 10 mg/ml HPβCD in a 1% w/v solution of poloxamer.

Example 12 (reference)

Preparation of nanoparticles of poly (isobutylcyanoacrylate) containing various active ingredients.

Solutions of hydrocortisone, prednisolone, spironolactone, testosterone, progesterone, danazol and megestrol acetate at concentrations corresponding to the saturation concentration in Poloxamer 188 (1% w/v) were separately added to the polymerization media. Nanoparticles of poly(isobutylcyanoacrylate) containing various active ingredients were then prepared as in Example 1, but in the absence of HPBCD.

Example 13

Titration of hydrocortisone, prednisolone, sipironolactone, testosterone, progesterone, danazol, meaestrol acetate and HPβCD.

The different steroids were determined as in Example 6 so that the titration of these different substances was conducted under the same analytical conditions.

The HPβCD was also titrated as in Example 6.

Example 14

Size and zeta potential characteristics of nanoparticles prepared according to the invention in the presence of absence of Poloxamer 188.

The nanoparticles prepared according to Example 11 and Example 12 were characterized as in Example 7. The size of the steroid-containing particles was generally smaller and close to approximately 100 nm when the nanoparticles of the invention were prepared in the absence of Poloxamer 188 and only in the presence of HPβCD, suggesting that the load contents were marked by the cyclodextrin molecules localized on the surface of the particles.

Table III below indicates the quantity of medicinal substance loaded by nanoparticles of poly(alkylcyanoacrylate) or nanoparticles of poly(alkylcyanoacrylate) and hydroxypropyl-β-cyclodextrin, and the corresponding cyclodextrin content (average of 3 values).

TABLE III

| Sample | | CD (mg/g) | Drug load (mg/g) |
|---|---|---|---|
| PIBCA | | | |
| PIBCA | hydrocortisone (HD) | — | 2.19 |
| | PE | — | 0.12 |
| | spironolactone (SP) | — | 7.65 |
| | testosterone (TE) | — | 2.27 |
| | megestrol acetate (AM) | — | 0.25 |
| | danazol (DA) | — | 0.34 |
| | progesterone (PO) | — | 0.79 |
| | IBCA/HPBCD | — | |
| PIBCA/HPBCB | HD | | 15.3 |
| | PE | | 15.5 |
| | SP | | 53.0 |
| | TE | | 19.5 |
| | AM | | 1.4 |
| | DA | | 11.2 |
| | PO | | 24.0 |

Results of Examples 11 to 14

Increase in the steroid content of nanoparticles according to the invention.

The values of steroid contents expressed in absolute value for the nanoparticles of the invention or the reference particles are grouped together in Table IV (average of three preparations). Calculation of the increase values in particle loads shows that the increase in content can reach 129 times for prednisolone.

TABLE IV

| Steroids | Content of PIBCA nanoparticles without HP CD (mmole/g) | Content of combined PIBCA and HP CD particles (mmole/g) | Increase in content load (number of times) |
|---|---|---|---|
| Hydrocortisone | 6.04 | 42.21 | 7.0 |
| Prednisolone | 0.33 | 43.00 | 129.2 |
| Spironolactone | 18.36 | 127.23 | 6.9 |
| Testosterone | 7.87 | 67.6 | 8.6 |
| Megestrolacetate | 0.65 | 3.64 | 5.6 |
| Danazol | 1.01 | 33.19 | 32.9 |
| Progesterone | 2.51 | 69.60 | 27.7 |

What is claimed is:

1. Nanoparticles comprising:
   at least one polymer;
   at least one active ingredient; and
   at least one cyclic oligosaccharide, wherein the active ingredient is largely contained in the nanoparticle matrix network and the cyclic oligosaccharide molecules are localized on the surface of the nanoparticles.

2. The nanoparticles according to claim 1, wherein at least one of the polymers is a poly(alkylcyanoacrylate) in which the alkyl group may be linear or branched and includes 1 to 12 carbon atoms.

3. The nanoparticles according to claim 1, wherein the cyclic oligosaccharide is a neutral or charged, native, branched or polymerized or chemically modified cyclodextrin.

4. The nanoparticles according to claim 1, wherein the cyclic oligosaccharide is a cyclodextrin chemically modified by substitution of one or more hydroxypropyls by alkyl, aryl, arylalkyl, glycosidic groups, or by etherification, esterification with alcohols or aliphatic acids.

5. The nanoparticles according to claim 1, having a size between about 300 and about 50 nm.

6. The nanoparticles according to claim 1, wherein the active ingredient is hydrophilic, hydrophobic, amphiphilic and/or insoluble.

7. The nanoparticles according to claim 1, wherein the active ingredient is selected from a group consisting of anticancer substances, antisense molecules, antivirals, antibiotics, proteins, polypeptides, polynucleotides, vaccinating substances, immuno-modulators, steroids, analgesics, antimorphinics, antifungals and antiparasitics.

8. The nanoparticles according to claim 1, wherein the active ingredient is taxol or one of its derivatives.

9. The nanoparticles according to claim 1, wherein the active ingredient is doxorubicin or one of its derivatives.

10. The nanoparticles according to claim 1, wherein the active ingredient is a derivative of platinum.

11. The nanoparticles according to claim 1, wherein the active ingredient is present in an amount of about 0.01 to about 300 mg/g nanoparticles.

12. The nanoparticles according to claim 1, wherein the proportion of cyclic oligosaccharide is from about 0.1 to about 70% by weight of the weight of the nanoparticles.

13. A method of preparing nanoparticles according to claim 1, comprising:
   a) preparing a complex of the at least one active ingredient with the at least cyclic oligosaccharide in solution in an aqueous or non-aqueous solvent,
   b) adding at least one monomer of the polymer in the solution obtained at step (a), and
   c) polymerizing the monomer, optionally, in the presence of one or more of a surfactant and/or stabilising agent.

14. A method for preparing nanoparticles according to claim 1, comprising:
   a) preparing nanoparticles by forming an inclusion complex of a poly(alkylcyanoacrylate) polymer, and a cylic oligosaccharide; and
   b) associating the active ingredient with the nanoparticles.

15. The method for preparing nanoparticles according to claim 7, further comprising:
   a) preparing a solution of at least one cyclic oligosaccharide in an aqueous or non-aqueous solvent;
   b) gradually adding at least an alkylcyanoacrylate monomer, to the solution of step (a);
   c) polymerizing the monomer in the presence of one or more of a surfactant and/or stabilising agent; and
   d) after control and optional purification of the nanoparticles obtained at step (c), incubating the nanoparticles in a solution of active ingredient in an aqueous or non-aqueous solvent.

16. The method for preparing nonparticles according to claim 13, wherein, at step (b), at least one alkylcyanoacrylate monomer is gradually added.

17. The method according to claim 13, wherein, at steps (a), (b) and (d), the solvent is selected such that, while maintaining conditions of polymerization of the polymers, the solubility of the active ingredient and of the cyclic oligosaccharide is maintained at a maximum.

18. The method according to claim 15, wherein step (c) is conducted with no surfactant and/or stabilizing agent.

19. The method according to claim 13, wherein, at step (a) the proportion of cyclic oligosaccharide is from about 0.1 to about 70% by weight relative to said active ingredient.

20. A medicinal product with targeted effect and improved therapeutic index produced by the method according to claim 15.

21. Nanoparticles obtained by the method according to claim 9.

22. Nanoparticles according to claim 21, wherein the cyclic oligosaccharide is selected from the group consisting of a neutral, a charged, a native, a branched, a polymerized, and a chemically modified cyclodextrin.

23. The nanoparticles according to claim 1, wherein the active ingredient combines itself with one or more cyclic oligosaccharides through the creation of low-energy chemical bonds.

24. The nanoparticles according to claim 1, wherein said nanoparticles further comprise a stabilizing and/or surfactant agent.

25. The nanoparticles according to claim 1, wherein the active ingredient is an antiviral.

* * * * *